| United States Patent [19] | [11] Patent Number: 4,554,358 |
| Takebe et al. | [45] Date of Patent: Nov. 19, 1985 |

[54] 4-CHLORO-4-METHYL-5-METHYLENE-1,3-DIOXOLANE-2-ONE

[75] Inventors: Yasushi Takebe, Tondabayashi; Koji Iuchi, Nara; Goro Tsukamoto, Toyonaka, all of Japan

[73] Assignee: Kanebo, Ltd., Tokyo, Japan

[21] Appl. No.: 675,922

[22] PCT Filed: Jun. 11, 1984

[86] PCT No.: PCT/JP84/00304

§ 371 Date: Nov. 16, 1984

§ 102(e) Date: Nov. 16, 1984

[87] PCT Pub. No.: WO85/00037

PCT Pub. Date: Jan. 3, 1985

[30] Foreign Application Priority Data

Jun. 14, 1983 [JP] Japan ................................ 58-107336

[51] Int. Cl.$^4$ ............................................ C07D 317/36
[52] U.S. Cl. .................................................... 549/229
[58] Field of Search ........................................ 549/229

[56] References Cited

U.S. PATENT DOCUMENTS 4,342,693  8/1982  Sakamoto et al. .................. 549/229

OTHER PUBLICATIONS

Fischler et al, Tetrahedron Letters, No. 17 (1972) pp. 1701-1704.

*Primary Examiner*—Norma S. Milestone
*Attorney, Agent, or Firm*—Millen & White

[57] ABSTRACT

4-Chloro-4-methyl-5-methylene-1,3-dioxolane-2-one is useful as an intermediate for the synthesis of 4-chloromethyl-5-methyl-1,3-dioxolene-2-one which, in turn, finds use as a modifying agent for making various prodrugs.

Said intermediate compound gives said objective compound in a good yield by a rearrangement reaction.

1 Claim, No Drawings

4-CHLORO-4-METHYL-5-METHYLENE-1,3-DIOXOLANE-2-ONE

TECHNICAL FIELD

This invention relates to 4-chloro-4-methyl-5methylene-1,3-dioxolane-2-one which is a novel intermediate for the synthesis of 4-chloromethyl-5-methyl-1,3-dioxolene-2-one which, in turn, finds use as a modifying agent for making various prodrugs.

BACKGROUND ART

There are a number of drugs which, owing to chemical instability and poor bioavailability, find only limited uses as a medicament though they have potentially high pharmacological activities. One of means for improving these defects is to provide prodrugs by chemically modifying these drugs.

Japanese Patent Publication (Kokai) No. 57-26684 discloses a useful modifying agent for making such prodrugs consisting of a 1,3-dioxolene-2-one derivative of the formula:

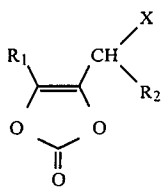

wherein $R_1$ is a hydrogen atom, a lower alkyl or aryl, X is a halogen atom, and $R_2$ is a hydrogen atom or a hydrocarbon chain forming a ring with $R_1$. Specific compounds disclosed therein include 4-chloromethyl-5-methyl-1,3-dioxolene-2-one of the formula:

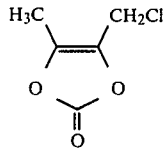

DISCLOSURE OF THE INVENTION

We have studied to provide a new method for preparing the above 4-chloromethyl-5-methyl-1,3-dioxolene-2-one (II). As a result, we have found that 4-chloro-4-methyl-5-methylene-1,3-dioxolane-2-one of the formula:

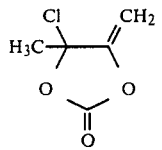

surprisingly gives said objective compound (II) in a good yield by a rearrangement reaction which will be fully described hereinafter and accomplished the present invention.

PREFERRED EMBODIMENT OF THE INVENTION

4-Chloro-4-methyl-5-methylene-1,3-dioxolane-2-one (III) of the present invention is a novel compound. This compound may be easily prepared by reacting 4,5-dimethyl-1,3-dioxolene-2-one of the formula:

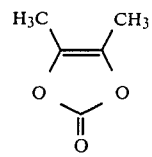

with a chlorinating agent in an inert organic solvent normally under an ionic reaction condition.

The starting compound (IV) used herein is a known compound and may be synthesized by the method, for example, described in *Tetrahedron Letters*, 1701–1704 (1972).

Examples of inert organic solvents include chlorinated organic solvents such as methylene chloride, chloroform, carbon tetrachloride, 1,2-dichloroethane and the like. Methylene chloride is most preferred.

Examples of chlorinating agents include sulfuryl chloride, chlorine gas and the like. Sulfuryl chloride is most preferred.

The molar ratio of chlorinating agent to the starting compound (IV) ranges preferably from about 0.9 to about 1.5, more preferably from about 1.0 to about 1.2. The use of chlorinating agent in amounts below said range or conversely in excess of said range results in a large amount of unreacted starting compound (IV) or a large amount of byproducts and thus is not preferable.

The reaction temperature ranges normally from 10° C. to 80° C., preferably from about 25° C. to about 60° C.

The reaction time may vary depending upon particular solvent and reaction temperature used and is generally from 30 minutes to 7 hours.

The compound (III) of this invention formed by the above-described reaction may be recovered and purified by a conventional method such as distillation in vacuo. Optionally, the reaction mixture containing the compound (III) may be used in the subsequent rearrangement reaction as such or after removing the solvent without isolating the compound (III).

Now the preparation of said 4-chloromethyl-5-methyl1,3-dioxolene-2-one (II) from the compound (III) of this invention will be described in detail.

The rearrangement of the compound (III) to the objective compound (II) may be carried out very easily by heating the compound (III) in the presence or absence of an inert organic solvent.

As examples of the above inert organic solvents, chlorinated organic solvents such as 1,2-dichloroethane, 1,1,2,2-tetrachloroethane and the like may be mentioned.

The heating temperature generally ranges from about 60° C. to about 140° C.

The reaction time may vary with particular temperature employed and is generally from about 1 hour to about 5 hours.

By effecting the rearrangement reaction under the above-described conditions, the compound (III) of the present invention may be converted to the objective compound (II) almost quantitatively.

The resulting objective compound (II may be isolated and purified in a good yield by a conventional method such as distillation in vacuo.

Thus, the compound (III) of this invention is useful as it is easily derived from the known compound (IV) and gives 4-chloromethyl-5-methyl-1,3-dioxolene-2-one (II), a useful drug-modifying agent.

The present invention will be more fully described by making reference to the following examples relating to the preparation of the compound (III) of this invention and 4-chloromethyl-5-methyl-1,3-dioxolene-2-one (II).

EXAMPLE 1

Preparation of 4-chloro-4-methyl-5-methylene-1,3-dioxolane-2-one (III)

To a solution of 50 g of 4,5-dimethyl-1,3-dioxolene-2-one (IV)(Synthesized by the method described in *Tetrahedron Letters*, 1701–1704 (1972)) in 350 ml of methylene chloride was added 65 g of sulfuryl chloride dropwise over 1 hour at 40°–42° C. The mixture was stirred for one hour at the same temperature and then evaporated in vacuo to remove the solvent. The resulting residue was distilled in vacuo to obtain 42.1 g (65% of theory) of 4-chloro-4-methyl-5-methylene-1,3-dioxolane-2-one (III) as a colorless oil.

B.p. 45°–48° C./2 mmHg.

IR(CHCl$_3$)$\nu$(cm$^{-1}$): 1820, near 1695 etc. NMR(CDCl$_3$, $\delta$(ppm)): 2.19(3H, s, CH$_3$),

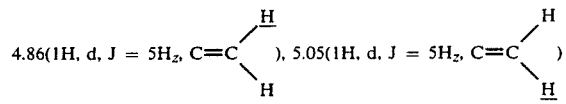

REFERENCE EXAMPLE 1

Preparation of 4-chloromethyl-5-methyl-1,3-dioxolene-2-one (II)

14 g of 4-chloro-4-methyl-5-methylene-1,3-dioxolane-2-one (III) prepared in Example 1 was heated at 90° C. with stirring for 2 hours. The resulting pale yellow oil was distilled in vacuo to obtain 11.7 g (84% of theory) of 4-chloromethyl-5-methyl-1,3-dioxolene-2-one (II) as a colorless oil.

B.p. 91°–93° C./2 mmHg.

IR(neat)$\nu$(cm$^{-1}$): 1820, near 1730 etc. NMR(CDCl$_3$, $\delta$(ppm)): 2.18(3H, s, CH$_3$), 4.31(2H, s, CH$_2$Cl).

REFERENCE EXAMPLE 2

Preparation of 4-chloromethyl-5-methyl-1,3-dioxolene-2-one (II)

To a solution of 75 g of 4,5-dimethyl-1,3-dioxolene-2-one (IV) in 750 ml of methylene chloride was added 97.6 g of sulfuryl chloride dropwise at 40°–42° C. over 2 hours. The mixture was stirred for 40 minutes at the same temperature and evaporated in vacuo to remove the solvent. NMR spectrometry of the resulting oil revealed that the product was 4-chloro-4-methyl-5-methylene-1,3-dioxolane-2-one (III) containing a trace amount of unreacted 4,5-dimethyl-1,3-dioxolene-2-one (IV). This oil was heated at 90° C. with stirring for 2 hours without isolating 4-chloro-4-methyl-5-methylene-1,3-dioxolane-2-one (III) and then distilled in vacuo. 75.4 g (corresponding to an overall yield from 4,5-dimethyl-1,3-dioxolene-2-one (IV) of 77%) of 4-chloromethyl-5-methyl-1,3-dioxolene-2-one (II) having the physicochemical properties described in Reference Example 1 was obtained.

INDUSTRIAL APPLICABILITY

According to the present invention, there is provided 4-chloro-4-methyl-5-methylene-1,3-dioxolane-2-one. This compound may be converted into 4-chloromethyl-5-methyl-1,3-dioxolene-2-one in a good yield by a rearrangement reaction for making various prodrugs using the latter compound as a modifying agent.

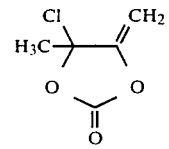

What is claimed is:

1. 4-chloro-4-methyl-5-methylene-1,3-dioxolane-2-one of the formula: